United States Patent [19]

Ueshima et al.

[11] Patent Number: 4,814,512
[45] Date of Patent: Mar. 21, 1989

[54] METHOD FOR THE PRODUCTION OF P-METHOXYBENZALDEHYDE

[75] Inventors: Michio Ueshima, Takarazuka; Yoshiyuki Takahashi, Suita; Masatoshi Tsuchino, Yokohama; Noboru Saito, Takatsuki, all of Japan

[73] Assignee: Nippon Shokubai Kagaku Kogyo, Osaka, Japan

[21] Appl. No.: 945,303

[22] Filed: Dec. 19, 1986

[30] Foreign Application Priority Data

Dec. 20, 1985 [JP] Japan .................. 60-285687
Dec. 20, 1985 [JP] Japan .................. 60-285688

[51] Int. Cl.⁴ .................... C07C 45/32; C07C 45/36
[52] U.S. Cl. ................................................ 568/432
[58] Field of Search ....................................... 568/432

[56] References Cited

U.S. PATENT DOCUMENTS 4,113,782 9/1978 Juichi et al. .
4,471,140 9/1984 Au .......................................... 568/432

FOREIGN PATENT DOCUMENTS 42974 3/1980 Japan .
85682 8/1980 Japan .
4012 11/1983 Japan .
78744 4/1986 Japan .................................. 568/432

Primary Examiner—Werren B. Lone
Attorney, Agent, or Firm—Omri M. Behr

[57] ABSTRACT

A method for the production of p-methoxybenzaldehyde by the vapor-phase catalytic oxidation of p-methoxytoluene, which method comprises cooling and condensing a mixed gas formed by said reaction of oxidation thereby preparing a solution containing p-methoxybenzaldehyde, treating said solution in the presence of at least one alkali selected from the group consisting of an alkali metal compound and an ammonium compound soluble in water and alkaline in nature, and subsequently distilling the resultant treated solution.

10 Claims, 1 Drawing Sheet

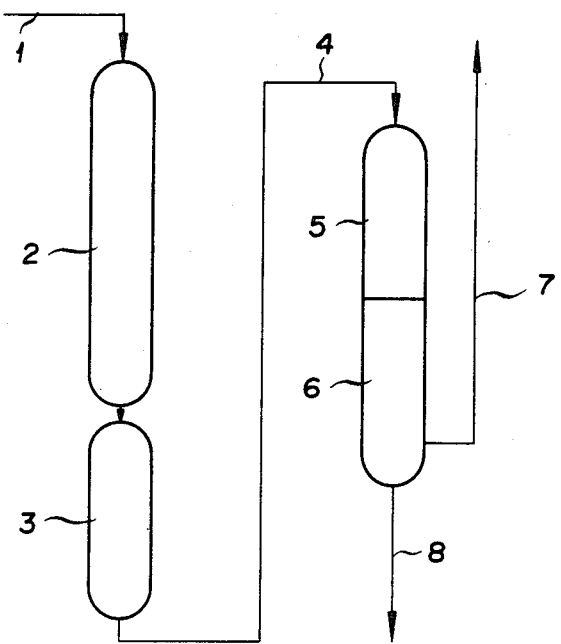

METHOD FOR THE PRODUCTION OF P-METHOXYBENZALDEHYDE

BACKGROUND OF THE INVENTION

1. Field of the Invention

This invention relates to a method for the production of p-methoxybenzaldehyde. More particularly, it relates to a method for the production of p-methoxybenzaldehyde by the vapor-phase catalytic oxidation of p-methoxytoluene, which method enables p-methoxybenzaldehyde to be produced with high quality.

2. Description of the Prior Art p-Methoxybenzaldehyde is a useful compound as perfume, brightener for metal plating, and raw material for medicines and has already found quantity consumption in various fields.

For the production of p-methoxybenzaldehyde from p-methoxytoluene, numerous methods have been proposed in the art. Generally, these methods effect the production of p-methoxybenzaldehyde by the liquid-phase reactions: (1) A method which produces p-methoxybenzaldehyde by effecting liquid-phase pressed oxidation of p-methoxytoluene with oxygen in the presence of a lower fatty acid with a soluble salt of manganese used as a catalyst (Japanese Patent Publication SHO 55(1980)-42,974) and (2) a method which produces p-methoxybenzaldehyde by electrolytically oxidizing p-methoxytoluene in the presence of a metal salt (Japanese Patent Laid-Open SHO 55(1980)-85,682) are typical examples.

These methods are invariably unsatisfactory because they have drawbacks of their own from the commercial and economic points of view. To be specific, the method of (1) is unsatisfactory because the yield of p-methoxybenzaldehyde is low and such steps of process as the control of reaction and the recovey of catalyst and solvent impose heavy burdens and the method of (2), though excellent in the yield of the product, is unsatisfactory because the economy of the process has much to be desired in connection with the recovery of the used catalyst, the efficiency of reuse of the recovered catalyst, and the cost of power. Another known method produces p-methoxybenzaldehyde by vapor-phase catalytic oxidation of p-methoxytoluene (Japanese Patent Publication SHO 58(1983)-4,012). This invention only discloses examples of this reaction.

The inventors formerly made a study in search of a method for the production of p-methoxybenzaldehyde by the vapor-phase catalytic oxidation and, consequently, developed a catalyst for producing p-methoxybenzaldehyde commercially advantageously in a high yield without entailing the aforementioned drawbacks (PCT/JP85/00628).

For the production of p-methoxybenzaldehyde by the vapor-phase catalytic oxidation, p-methoxytoluene and a molecular oxygen-containing gas (such as, for example, air) are substantially all the raw materials required. Absolutely no organic solvent is used at any step in the whole production process. The waste liquid occurring in the process at all is practically the whole volume of the water formed by the reaction. Even from the standpoint of the disposal of this waste liquid for the prevention of environmental pollution, this process is highly advantageous both commercially and economically.

When p-methoxytoluene is oxidized in a vapor-phase, however, various by-products occur though in small amounts in addition to the principal product aimed at. It has been demonstrated that these by-products impair the quality of p-methoxybenzaldehyde and that this impaired quality cannot be mended merely by ordinary distillation.

When the aforementioned catalyst is used in the vapor-phase catalytic oxidation of p-methoxytoluene with molecular oxygen or a molecular oxygen-containing mixed gas at elevated temperatures, the conversion of p-methoxytoluene is heightened, the product aimed at, i.e. p-methoxybenzaldehyde, is obtained in high yield and high selectivity, no solvent is required at any step in the whole production process, and the expense for the disposal of the waste liquid from the process is small. Thus, the process proves to be highly satisfactory from the commercial point of view.

Further, when the reaction is carried out in the form of vapor-phase catalysis, the reaction can be effected by a continuous operation, the heat evolved by the oxidation can be recovered by being utilized in heat-exchanging the vapor, and the cost of production can be notably lowered. Thus, the continuous method proves to be highly satisfactory from the economic point of view as well. In this reaction, however, since the product of the oxidation is discharged in the form of a gas of very high temperature from the reaction system, development of a method for efficient collection of the emanating gaseous product poses itself a problem.

Generally, p-methoxybenzaldehyde by nautre is spontaneously oxidized by the oxygen in the air when it is left standing in the air and readily converted into p-methoxybenzoic acid.

When the p-methoxybenzaldehyde produced is in the form of a mixed gas discharged at an elevated temperature from the system of the vapor-phase oxidation, it is gradually oxidized into p-methoxybenzoic acid. The crystals of this acid bring about numerous difficulties such as the clogging of the piping, the hindrance to the operation of the apparatus, and the substantial decrease of the yield of the product during the isolation.

An object of this invention, therefore, is to provide a method for the production of p-methoxybenzaldehyde of high purity.

Another object of this invention is to provide a method for the production of p-methoxybenzaldehyde of high purity by the vapor-phase catalytic oxidation of p-methoxy-toluene.

Yet another object of this invention is to provide a method for the production of p-methoxybenzaldehyde of high purity in a high yield by the vapor-phase catalytic oxidation of p-methoxytoluene.

SUMMARY OF THE INVENTION

The objects described above are accomplished by a method for the production of p-methoxybenzaldehyde by the vapor-phase catalytic oxidation of p-methoxytoluene, which method comprises cooling and condensing a mixed gas formed by the oxidation thereby producing a solution containing p-methoxybenzaldehyde, treating this solution in the presence of at least one alkali selected from the group consisting of an alkali metal compound and an ammonium compound, soluble in water and alkaline in nature, and subsequently distilling the product of this treatment.

BRIEF DESCRIPTION OF THE DRAWING

The drawing is a flow sheet illustrating a preferred embodiment of the process for the production of p-methoxybenzaldehyde in accordance with the method of this invention.

DESCRIPTION OF THE PREFERRED EMBODIMENT

The method contemplated by this invention for the production of p-methoxybenzaldehyde comprises subjecting p-methoxytoluene to catalytic oxidation in a vapor phase with a molecular oxygen-containing gas thereby producing a mixed gas containing the product of the oxidation, cooling and condensing the mixed gas thereby giving rise to a solution containing p-methoxybenzaldehyde, treating the solution in the presence of at least one alkali selected from the group consisting of an alkali metal compound and an ammonium compound soluble in water and alkaline in nature, and subsequently distiling the treated solution.

The vapor-phase catalytic oxidation of p-methoxytoluene can be effected by any of the known methods such as, for example, the method of the inventors' own development disclosed in PCT/JP85/00628, which comprises effecting vapor-phase catalytic oxidation of the compound in question with a molecular oxygen-containing gas in the presence of a catalytic composition represented by the formula, $V_a X_b Y_c O_d$ [wherein X stands for at least one element selected from the group consisting of Na, K, Rb, Cs, and Tl (except for single use of K), Y for at least one element selected from the group consisting of Mg, Ca, Sr, Ba, Nb, Ta, P, Sb, Bi, Cu, Ag, Ti, Fe, Co, Ni, Sn, Ce, and Zn, and a, b, c, and d stand for atomic ratios of the respective elements that where a=1 is assumed, b has a value in the range of 0.1 to 5, c has a valve in the range of 0 to 5, and d has a value determined by the valen cies of the other elements and the value of said atomic ratio.]

The crude p-methoxybenzaldehyde obtained by the vapor-phase catalytic oxidation entrains minute amounts of p-methoxybenzoic acid, quinone derivatives, and substances of unidentifiable structures in addition to a small amount of unaltered p-methoxytoluene. Because of the inclusion of the small amounts of by-products, the crude p-methoxybenzaldehyde assumes a very slight reddish brown color.

The alkali metal compounds which are usable for the treatment of the crude p-methoxybenzaldehyde solution are water-soluble carbonates, hydroxides, phosphates, alcoholates, etc. Typical examples of such alkali metal compounds include sodium carbonate, sodium hydrogen carbonate, sodium hydroxide, sodium phosphate, potassium carbonate, potassium hydrogen carbonate, potassium hydroxide, potassium phosphate, lithium carbonate, lithium hydrogen carbonate, lithium hydroxide, lithium phosphate, sodium methylate, sodium ethylate, sodium isopropoxide, potassium methylate, potassium ethylate, and potassium isopropoxide. The other water-soluble salts of alkai metals are similarly usable advantageously. Among other compounds enumerated above, sodium and potassium compounds prove particularly desirable.

The ammonium compounds usable for the treatment are ammonia, ammonium hydroxide, ammonium carbonate, ammonium phosphate, etc. Other basic water-soluble ammonium compounds are similarly usable advantageously. These are invariably alkaline compounds.

The effect of this treatment contemplated by this invention is not obtained by using an acidic or neutral compound. The amount of the water-soluble compound to be used for the treatment is variable with the amounts of by-products entrained in the crude p-methoxybenzaldehyde. In consideration of the cost of production, this amount is desired to be as small as permissible. Generally, it falls in the range of 1 to 20% by weight, preferably 2 to 10% by weight.

The amount of the water to be used for dissolving the water-soluble compound is not specifically defined. The amount of water produced by the reaction of oxidation can be utilized sufficiently for this purpose. Specifically, the treatment can be ampy effectively carried out by leaving the water formed by the reaction unseparated during the fractional separation of the crude p-methoxybenzaldehyde, dissolving the alkaline compound in the remaining water, and stirring the crude p-methoxybenzaldehyde in the resulting solution at room temperature. In this case, the waste liquid which occurs in the process of production at all is the whole amount of the water formed by the reaction of oxidation. Thus, this practise of utilizing the water formed by the reaction proves to be high advantageous ecomonically.

As a modification of the method of this invention, during the collection of the formed gas issuing from the vapor-phase catalytic oxidation through the treatment of cooling and condensing, the alkaline compound under discussion may be dissolved in the cooling water being used for direct contact cooling. The condensate of the crude p-methoxybenzaldehyde is obtained at a temperature not exceeding 100° C., particularly falling in the range of 0° to 50° C. The alkaline compound is thoroughly mixed within the collected condensate and fed to the subsequent steps of separation and purification.

The conditions for the addition of the alkaline compound to the crude p-methoxybenzaldehyde solution are not specifically defined. The incorporation of the alkaline compound in the solution can be obtained effectively by thoroughly stirring the added alkaline compound in the solution at room temperature.

Subsequently, the aqueous layer is separated from the oil layer. The crude p-methoxybenzaldehyde treated as described above and now contained in the separated oil layer is separated by distillation of the oil layer and purified. For this distillation is used an ordinary vacuum distillation device comprising a column and a packing material filling the interior of the column. The distillation is performed under a blanket of an inert gas. Examples of the inert gas usable therefor include nitrogen, argon, and carbon dioxide gas. Inclusion of molecular oxygen such as, for example, air in the inert atmosphere is undesirable because the oxygen induces gradual oxidation to p-methoxybenzoic acid during the course of distillation and the crystals of this acid are deposited on the packing material in the column possibly to the extent of lowering the yield and clogging the column and consequently jeopardizing the operation of the reaction.

The operation of distillation is carried out in three steps, the first step for the removal of the unaltered p-methoytoluene, the second step for the removal of the mixture of p-methoxytoluene and p-methoxybenzaldehyde, and the third step for the isolation of p-methoxybenzaldehyde. The p-methoxytoluene removed in the first step is reclaimed as the raw material for the reaction of oxidation and the mixture removed in the second step is returned as the raw material for redistillation.

Thus, the otherwise possible loss of yield can be reduced to a great extent.

The p-methoxybenzaldehyde which is purified by the method of the present invention enjoys an extremely high quality such that the purity is not less than 99.7% by weight and the color (APHA) is not higher than 20.

In accordance with the present invention, the production of p-methoxybenzaldehyde by the vapor-phase oxidation of p-methoxytoluene is accomplished by a method which comprises (I) a step of causing the reaction of oxidation, (II) a step of cooling the reaction gas emanating from the foregoing step of reaction thereby inhibiting the otherwise inevitable gradual oxidation of p-methoxybenzaldehyde into p-methoxybenzoic acid, and (III) a step of condensing the product selectively from the cooled reaction gas and collecting the condensate. Thus, the method of this invention manifests a significant effect of enabling the p-methoxybenzaldehyde formed in the step (I) for the reaction of oxidation to be collected efficiently without entailing the gradual oxidation thereof and without suffering from any appreciable loss of yield.

A typical embodiment of this invention will be described specifically below with reference to the accompanying drawing.

A mixed gas comprising p-methoxytoluene and a molecular oxygen-containing gas is introduced via a pipe 1 into the step (I) for the reaction of oxidation. This step comprises the operation of a reactor packed with the specific catalyst and kept at an elevated temperature (in the range of 300° to 500° C., preferably 350° to 450° C. In this step, the p-methoxytoluene in the mixture is oxidized and converted into p-methoxybenzaldehyde. Although the conversion of p-methoxytoluene in this reaction is not specifically defined, it is desired to be not less than 80 mol % in consideration of the cost of recovery of the unaltered p-methoxytoluene during the course of the purification.

The heat which is evolved in the step for the reaction of oxidation is generally utilized as the source of heat for the reactor so that this reactor has substantially no use for external supply of heat. When the amount of the heat thus generated by the reaction exceeds that which is required for keeping the reactor at a necessary temperature and for radiation from the reactor and, therefore, requires to be forcibly released from the reaction system, the heat medium of the reactor is circulated through a waste heat boiler, there to effect recovery of heat through conversion of the heat into vapor.

Then, the hot gas produced by the reaction and released from the reactor 2 is introduced into the step of (II) for cooling. A cooler 3 used for this step is a tubular cooler, which is disposed at as small a distance as possible from the reactor 2 and connected to the reactor 2. During the course of this cooling treatment, the gaseous p-methoxybenzaldehyde formed in the preceding step must be inhibited from auto-oxidation. First, the cooling temperature which depends, though not exclusively, on the concentration of the gas fed as the raw material, is desired to be higher than the temperature at which p-methoxybenzaldehyde is condensed and specifically to fall in the range of 100° to 200° C. Any cooling temperature below the lower limit of the range is undesirable because, at such a low cooling temperature, the p-methoxybenzaldehyde is partially deposited in the form of a condensate at the outlet of the condenser and in the pipe leading to the subsequent step and the condensate after protracted stagnation is converted into p-methoxybenzoic acid to clog the pipe and render the continuous reaction difficult.

The residence time in the cooling step (II) of the gas resulting from the reaction has only to be enough to effect thorough cooling of the gas. Though the length of the residence time is not critical, it is desired to be in the range of 0.05 to 10 seconds, preferably 0.1 to 5 seconds. This cooling step (II) is operated in a packed column type or multi-tube type condenser which is kept at a temperature incapable of inducing condensation of p-methoxybenzaldehyde.

Again for the prevention of the condensation, a pipe 4 emanating from the cooling step (II) and leading to the subsequent condensing and collecting step (III) is desired to be kept at a temperature in the range of 100° to 200° C., preferably 120° to 170° C.

The cooled reaction gas forwarded through the pipe 4 is introduced into the step (III) of condensation and collection which comprises condensers 5, 6, wherein the p-methoxybenzaldehyde, the unaltered p-methoxytoluene, formed water, and small amounts of by-products contained in the reaction gas are condensed and collected. The condensers 5, 6 are formed of ordinary multi-tube condensers or packed column type condensers. The condenser 5 is cooled with water and the condenser 6 is cooled with a coolant such as brine.

The reaction gas which has been introduced into the condensers 5, 6 is cooled in this step to a temperature in the range of 0° to 50° C., preferably 0° to 30° C. Any cooling temperature below the lower limit of the range just mentioned has a disadvantage that p-methoxybenzaldehyde or the water of the reaction is frozen, for example. Conversely any cooling temperature above the upper limit of the range is undesirable because the amounts of p-methoxybenzaldehyde and p-methoxytoluene suffered to drift into the waste gas are increased to cause a loss of the yield. The waste gas remaining after the collection of the product is released from the system via a tube 7 and then disposed of as in a waste gas incinerator.

The collected liquid thus obtained is a two-phase liquid containing an oil layer containing p-methoxybenzaldehyde, a small amount of p-methoxytoluene, and minute amounts of by-products and an aqueous layer containing a very small amount of fatty acids. These two layers are separated in the subsequent purification step for purification of the product.

The method of this invention is highly effective in producing p-methoxybenzaldehyde by the vapor-phase catalytic oxidation. In the crude p-methoxybenzaldehyde obtained in consequence of the vapor-phase catalytic oxidation, very minute amounts of p-methoxybenzoic acid, quinone derivatives, and substances of unidentifiable structure are contained besides the unaltered p-methoxytoluene. These minute amounts of by-products are responsible for impairment of the quality of the product p-methoxybenzaldehyde. Particularly the quinone derivatives and the substances of unidentifiable structure cannot be thoroughly removed from the crude solution by the treatment of distillation and require a pretreatment of some sort. When the crude p-methoxybenzaldehyde is subjected to distillation instead of being treated as contemplated by the present invention, the produced p-methoxybenzaldehyde suffers from heavy coloration and attains purity only to the level of about 99% by weight. Moreover this crude p-methoxybenzaldehyde induces heavy deposition of a tarry colored substance on the packing material during the treatment of distillation and prevents the operation from being continued for a long time.

The water-soluble and alkaline compound to be used in this invention has an effect of converting such substances which are detrimental to the refining treatment into water-soluble substances and facilitating separation of these substances from the only solution of the crude p-methoxybenzaldehyde. When this pretreatment is carried out and then the treatment of distillation is performed, the phenomenon of coloration and the accumulation of a deposit on the packing material which are described above are not observed at all. Thus, the isolation of p-methoxybenzaldehyde can be attained with ease.

For use in this treatment, the water generated by the reaction of oxidation is utilized. Thus, the method of this invention is additionally effective in greatly lessening the burden imposed on the disposal of the waste water. Thus, this invention provides a simple and economical method.

Further, when the method of this invention is carried out by the procedure which comprises (I) the step of effecting the reaction of oxidation, (II) the step of cooling the reaction gas emanating from the step of reaction thereby inhibiting the otherwise inevitable gradual oxidation of p-methoxybenzaldehyde to p-methoxybenzoic acid, and (III) the step of condensing the cooled gas thereby collecting the product in the form of condensate, the raw materials required for the production of p-methoxybenzaldehyde are substantially only p-methoxytoluene and a molecular oxygen-containing gas (such as, for example, air) and the production of p-methoxybenzaldehyde can be attained efficiently without requiring use of any solvent. Moreover, the amount of the waste liquid is such as to be ascribable to the amount of the water produced by the reaction and, therefore, the cost of the disposal of the waste liquid is extremely small.

The heat generated by the reaction in the step (I) for the reaction of oxidation at times can be recovered in the form of steam and, practically, the cost otherwise required for heating the reactor is not required in the method of this invention. Thus, this method accomplishes the production of p-methoxybenzaldehyde highly advantageously from the economic point of view.

In accordance with the method of production contemplated by this invention, by cooling the reaction gas issuing from the reaction of oxidation to a temperature in the prescribed range, the gradual oxidation of the produced p-methoxybenzaldehyde into p-methoxybenzoic aicd can be completely inhibited so that the yield is not impaired at all and the yield of the production is highly satisfactory. If the step of (II) for the cooling of the reaction gas is omitted from the procedure described above, the p-methoxybenzaldehyde contained in the reaction gas emanating from the reactor 2 is partially oxidized gradually into p-methoxybenzoic acid and, at the same time, the crystals of the p-methoxybenzoic acid are deposited in the condenser being operated in the subsequent step (III) for condensation and collection of the product possibly so much as to obstruct the operation. Further, in the step of collection of the product, the reaction gas undergoes the phenomenon of conversion into fume and the greater part of the p-methoxybenzaldehyde is suffered to escape collection and diffuse into the ambient air to entail a serious loss of the yield.

This fact clearly shows that the method of production contemplated by this invention is greatly efficient and advantageous from the commercial and economic points of view.

Now, the present invention will be described more specifically below with reference to working examples.

EXAMPLE 1

To about 20 ml of hot water, 1.07 kg of ammonium metavanadate was added and a solution of 716 g of cesium nitrate and 445 g of copper nitrate in about 5 liter of water was added. They were stirred at 70° C. for about 1 hour. The resulting mixture and 624 g of Cellite (trademark designation) added thereto were concentrated by evaporation. The concentrated mixture was dried first at 120° C. for about 2 hours and then at 220° C. for 16 hours. Then, the dried mixture was calcined at 600° C. for 6 hours. The resultant calcined mass was molded in the form of beads 6 mm in diameter. The catalyst thus obtained was placed to fill a reaction tube 25.4 mm in diameter and 2000 mm in length and heated to 410° C. by the use of molten salt as a heat medium. Through this reaction tube, a mixed gas containing 2% by volume of p-methoxytoluene and 98% by volume of air was continuously passed as the raw material at a space velocity of 3,000 hr$^{-1}$. The mixed gas emanating from the reaction tube was cooled and condensed to collect 3.2 kg of condensate. This condensate was a liquid containing an oil layer (crude p-methoxybenzaldehyde) composed mainly of p-methoxybenzaldehyde and an aqueous layer formed of the water of the reaction.

By analysis, 3.2 kg of the condensate was found to contain 2.3 kg of p-methoxybenzaldehyde and 0.6 kg of the water of the reaction. In a vessel, this condensate was heated to 50° C. and stirred and 60 g of sodium carbonate was simultaneously added thereto and then stirred for 30 minutes. The resulting mixture was left cooling and separating into an oil layer and an aqueous layer.

Subsequently, the oil layer was introduced into a distillation column and subjected therein to a treatment of distillation for recovery of p-methoxytoluene and purification of p-methoxybenzaldehyde.

The distillation column was a packed column 50 mm in inside diameter and 1,000 mm in length and it was packed with Dixon packing 6 mm in particle diameter. The interior of the column was kept under a vacuum of 30 mmHg with nitrogen gas and the bottom of the column was heated to effect distillation under reflux. As the initial distillate, unaltered p-methoxytoluene containing a small amount of water. This distillate was put to re-use as the raw material for the reaction of oxidation. At this time, the temperature of the bottom in the column was 145° C. and the column top temperature was 87° C. Then, under the same conditions, the column top temperature was heightened from 87° C. to 145° C. to effect distillation of a mixture of p-methoxytoluene and p-methoxybenzaldehyde. This mixture was put to re-use as the raw material for distillation. Then, ample distillation of p-methoxytoluene was confirmed by analysis using gas chromatography, distillation of the product p-methoxybenzaldehyde was started (column bottom temperature 152° C. and the column top temperature 147° C.)

Consequently, 2.07 kg of p-methoxybenzaldehyde was obtained. This was a transparent colorless liquid of high quality, having a purity of 99.8% by weight and a color (APHA) of 10.

The series of steps mentioned above was repeated 10 times, to obtain p-methoxybenzaldehyde of high quality stably in each of the cycles. Even after 10 cycles of the operation, absolutely no accumulation of deposit was observed on the packing.

EXAMPLE 2-8

The procedure of Example 1 was repeated, except that the compounds used for the treatment were changed to those indicated in Table 1 without changing the amounts to be used. The results were as shown in Table 1. In each of the examples, the series of steps was repeated three times instead.

In any of the examples, absolutely no accumulation of a deposit was observed on the packing during the course of operation.

Controls 1-2

The procedure of Example 1 was repeated, except that the compounds used for the treatment were changed to neutral or acidic compounds indicated in Table 1 without changing the amounts thereof to be used. The results were as shown in Table 1. From the data, it is noted that the products were unsatisfactory in terms of purity and color. Particularly, they were heavily colored. In each of the experiments, accumulation of a deposit on the packing inside the distillation column was observed within one cycle of the treatment.

Control 3

The procedure of Example 1 was repeated, except that the distillation alone was carried out and the outer treatments were omitted. The results were as shown in Table 1. The product was heavily colored. A heavy accumulation of a deposit was observed on the packing within one cycle of the distillation.

TABLE 1

| Example | Compound used for treatment | Purity of p-methoxybenzaldehyde (% by weight) | Color (APHA) |
| --- | --- | --- | --- |
| Example 2 | NaHCO$_3$ | 99.7 | 15 |
| Example 3 | Na$_3$PO$_4$ | 99.9 | 5 |
| Example 4 | NaOH | 99.8 | 10 |
| Example 5 | K$_3$PO$_4$ | 99.7 | 15 |
| Example 6 | KOH | 99.8 | 5 |
| Example 7 | (NH$_4$)$_2$CO$_3$ | 99.7 | 15 |
| Example 8 | (NH$_4$)$_2$HPO$_4$ | 99.7 | 10 |
| Control 1 | KNO$_3$ | 98.9 | min. 300 |
| Control 2 | KHSO$_4$ | 99.0 | min. 300 |
| Control 3 | none | 98.8 | min. 500 |

EXAMPLE 9

Spherical catalyst possessing a composition of $V_{1.0}Cs_{0.4}Cu_{0.2}$ and measuring 6 mm in diameter which were prepared by following the procedure of Example 1 were placed to fill a stainless steel reaction tube 25.4 mm in inside diameter and 2,000 mm in length and heated to 410° C. with a molten salt as a heat medium. Through the reaction tube, a mixed gas containing 2% by volume of p-methoxytoluene and 98% by volume of air was continuously passed at a space velocity of 3,000 hr$^{-1}$.

In this operation, the conversion of p-methoxytoluene was 90.6 mol % and the yield and selectivity of p-methoxybenzaldehyde were respectively 73.3 mol % and 80.9 mol % per pass through the catalyst bed. As by-products, small amounts of CO, p-methoxybenzoic acid, and other carboxylic acid compounds besides $CO_2$ were found to be formed. The temperature of the reaction gas at the outlet of the reaction tube was 413° C.

The reaction gas emanating from the step (I) of reaction was introduced into a stainless steel cooling tube 25.4 mm in diameter and 1,000 mm in length packed with ceramic raschig rings ¼ inch in diameter and was cooled to 150° C. by circulating a heat medium at 150° C. outside the tube and fixing the retention time at 0.6 second. By the analysis of the cooled reaction gas, the yield of p-methoxybenzaldehyde was found to be 73.2 mol % and the content of p-methoxybenzoic acid in the by-products was substantially the same as that at the outlet of the reactor 2, indicating that absolutely no gradual oxidation of p-methoxybenzaldehyde occurred during the treatment.

The reaction gas which had been cooled to the cooling step (II) was passed through the tube 4 kept at 150° C. and introduced into the cooling tube of a condensing collector (5, 6). The collector (5, 6) was a condenser formed of four stainless steel tubes 20 mm in inside diameter and 2,000 mm in length and was adapted so that the upper part and the lower part thereof were cooled with coolants of different temperatures. The upper part 5 was cooled with service water and the lower part 6 with brine respectively.

The reaction gas departing from the tube 4 at 150° C. was cooled in the upper and lower parts 5, 6 to 5° C. so that p-methoxybenzaldehyde, p-methoxytoluene, formed water, and very small amounts of by-products contained in the formed gas were substantially completely condensed and collected. In the gas which had escaped condensation, $CO_2$ was a main component besides air and a very small amount of CO and very minute amounts of p-methoxybenzaldehyde and p-methoxytoluene commensurate with the vapor pressure at the prevalent temperature. Absolutely no diffusion of either p-methoxybenzaldehyde or p-methoxytoluene due to the phenomenon of conversion into fuse was observed.

Then, 3.2 kg of the condensate consequently obtained and 60 g of sodium carbonate incorporated therein were treated and distilled by following the procedure of Example 1. The p-methoxybenzaldehyde thus obtained was a transparent colorless liquid of very satisfactory quality, having a purity of 99.8% by weight and a color (APHA) of 10.

The complete process ranging from the step (I) through the step (III) was continuously operated for six months under the conditions shown mentioned above. During the course of the continuous operation, absolutely no increase of p-methoxybenzoic acid was observed and no clogging of the pipe interiors was found. Thus, p-methoxybenzaldehyde could be produced in a high yield stably.

Control 4

The procedure of Example 1 was repeated, except that the condenser 3 was omitted from the cooling step (II). The reaction gas emanating at 413° C. from the reactor 2 was passed through the tube 4 kept heated directly at 150° C. and introduced into the condensing collector 5, 6 to effect continuous operation. Consequently, needle crystals of p-methoxybenzoic acid were deposited in a large amount near the entrance to the column 5. In about two weeks' continued operation, the interior of the condensing collector was clogged so heavily as to render further operation difficult.

During the course of this continued operation, the phenomenon of conversion of the reaction gas into fume was observed to occur in the cooling part of the column 5, 6. When the gas diffusing from the tube 7 was analyzed, it was confirmed that 5.4% by weight of the p-methoxybenzaldehyde produced in the step (I) of reaction had been lost through diffusion.

What is claimed is:

1. A method for the purity enhancement of p-methoxybenzaldehyde produced by the vapor-phase catalytic oxidation of p-methoxytoluene with an oxygen containing gas, which comprises cooling and condensing a mixed gas formed by said oxidation reaction to form a solution containing p-methoxybenzaldehyde, treating said solution in the presence of at least on alkali selected from the group consisting of a water soluble alkali metal compound and an alkaline water soluble ammonium compound and subsequently distilling the resultant treated solution.

2. A method according to claim 1, wherein the amount of said alkali is in the range of 1 to 20% by weight, based on the amount of p-methoxybenzaldehyde.

3. A method according to claim 1, wherein said alkali metal compound is at least one compound selected from the group consisting of carbonates, hydroxides, phosphates, and alcoholates of alkali metals.

4. A method according to claim 3, wherein said alkali metal is sodium or potassium.

5. A method according to claim 4, wherein said alkali metal compound is at least one compound selected from the group consisting of sodium carbonate, sodium hydrogen carbonate, sodium hydroxide, sodium phosphate, sodium alcoholate, potassium carbonate, potassium hydrogen carbonate, potassium hydroixde, potassium phosphate, and potassium alcoholate.

6. A method according to claim 1, wherein said ammonium compound is at least one member selected from the group consisting of ammonia, ammonium hydroxide, ammonium carbonate, and ammonium phosphate.

7. A method according to claim 1, wherein said solution containing p-methoxybenzaldehyde is obtained by a procedure comprising (I) a step of subjecting p-methoxytoluene to vapor-phase catalytic oxidation, (II) a step of cooling the reaction gas emanating from said step of reaction to a temperature not lower than the condensing temperature of p-methoxybenzaldehyde, and (III) a step of condensing and collecting the reaction product from the cooled reaction gas.

8. A method according to claim 7, wherein the cooling temperature in said (II) cooling step is in the range of 100° to 200° C.

9. A method according to claim 7, wherein the retention time of said reaction gas in said (II) cooling step is in the range of 0.05 to 10 seconds.

10. A method according to claim 7, wherein the condensing temperature in the (III) condensing and collecting step is in the range of 0° to 50° C.

* * * * *